United States Patent
Wang et al.

(10) Patent No.: US 11,938,139 B2
(45) Date of Patent: *Mar. 26, 2024

(54) PHARMACEUTICAL COMPOSITIONS AND METHODS FOR ANXIETY, DEPRESSION AND OTHER PSYCHIATRIC DISORDERS

(71) Applicant: LA PharmaTech Inc., Blacksburg, VA (US)

(72) Inventors: Jianmin Wang, Blacksburg, VA (US); Geping Cui, Beijing (CN)

(73) Assignee: LA PharmaTech Inc., Blacksburg, VA (US)

( * ) Notice: Subject to any disclaimer, the term of this patent is extended or adjusted under 35 U.S.C. 154(b) by 180 days.

This patent is subject to a terminal disclaimer.

(21) Appl. No.: 16/884,459

(22) Filed: May 27, 2020

(65) Prior Publication Data

US 2020/0323876 A1    Oct. 15, 2020

Related U.S. Application Data

(63) Continuation-in-part of application No. 16/382,885, filed on Apr. 12, 2019, now Pat. No. 10,966,989.

(51) Int. Cl.
*A61K 31/5517* (2006.01)
*A61K 9/00* (2006.01)

(52) U.S. Cl.
CPC ........ *A61K 31/5517* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 4,871,733 A | 10/1989 | Sunshine et al. | |
| 5,068,233 A | 11/1991 | Achterrath-Tuckerman et al. | |
| 5,086,050 A | 2/1992 | Hettche et al. | |
| 5,110,814 A * | 5/1992 | Engel | A61P 17/06 514/217.05 |
| 5,430,029 A | 7/1995 | Biella et al. | |
| 5,958,964 A | 9/1999 | Pappolla | |
| 5,994,357 A | 11/1999 | Theoharides | |
| 6,017,909 A | 1/2000 | Hettche et al. | |
| 6,849,621 B2 | 2/2005 | Rosenblum et al. | |
| 7,022,687 B1 | 4/2006 | Szelenyi et al. | |
| 7,220,735 B2 | 5/2007 | Ting et al. | |
| 7,355,042 B2 | 4/2008 | Edgar et al. | |
| 7,615,550 B2 | 11/2009 | Heightman et al. | |
| 7,786,161 B2 | 8/2010 | Tani et al. | |
| 8,071,073 B2 | 12/2011 | Dang et al. | |
| 8,168,620 B2 | 5/2012 | Lulla et al. | |
| 8,168,625 B2 | 5/2012 | Vandoni et al. | |
| 8,304,405 B2 | 11/2012 | Lulla et al. | |
| 8,318,709 B2 | 11/2012 | Lulla et al. | |
| 8,518,919 B2 | 8/2013 | Dang et al. | |
| 8,741,319 B2 | 6/2014 | Crain et al. | |
| 8,758,816 B2 | 6/2014 | Fuge et al. | |
| 8,859,531 B2 | 10/2014 | Lee et al. | |
| 8,865,733 B2 | 10/2014 | Felder | |
| 9,119,846 B2 | 9/2015 | Zisapel et al. | |
| 9,278,092 B2 | 3/2016 | Chase et al. | |
| 9,308,212 B2 | 4/2016 | Los | |
| 9,700,548 B2 | 7/2017 | Knutsen et al. | |
| 9,901,585 B2 | 2/2018 | Lulla et al. | |
| 9,919,050 B2 | 3/2018 | Dang et al. | |
| 10,045,915 B2 | 8/2018 | Glenn, Jr. et al. | |
| 10,639,314 B1 | 5/2020 | Wang et al. | |
| 10,639,315 B1 | 5/2020 | Wang et al. | |
| 10,639,316 B1 | 5/2020 | Wang et al. | |
| 10,682,343 B2 | 6/2020 | Hand et al. | |
| 10,898,493 B2 | 1/2021 | Wang et al. | |
| 10,946,026 B2 | 3/2021 | Wang et al. | |
| 10,966,989 B2 | 4/2021 | Wang et al. | |
| 11,116,773 B2 | 9/2021 | Wang et al. | |
| 11,318,144 B2 | 5/2022 | Wang et al. | |
| 11,351,179 B1 | 6/2022 | Wang et al. | |

(Continued)

FOREIGN PATENT DOCUMENTS

| | | |
|---|---|---|
| AU | 2019443520 A1 | 12/2021 |
| AU | 2019445048 A1 | 12/2021 |

(Continued)

OTHER PUBLICATIONS

Hashiro et al. "A Combination Therapy of Psychotropic Drugs and Antihistaminics or Antiallergics in Patients with Chronic Urticaria". Journal of Dermatological Sciences. 1996; 11:209-213. (Year: 1996).*

(Continued)

*Primary Examiner* — Leslie A. Royds Draper

(74) *Attorney, Agent, or Firm* — New River Valley IP Law, P.C.; Michele L. Mayberry; Ashley M. Gates

(57) ABSTRACT

Pharmaceutical compositions comprising azelastine or a pharmaceutically acceptable salt of azelastine and alprazolam are disclosed. Methods of using the pharmaceutical compositions for treating patients suffering from one or more psychiatric disorders such as major depressive disorder, generalized anxiety disorder, panic disorder, agitation, social anxiety disorder, mild chronic depression, obsessive-compulsive disorder, premenstrual dysphoric disorder, seasonal affective disorder, dysthymia, childhood enuresis, bipolar disorder, posttraumatic stress disorder, sleep disorder related to anxiety, are also disclosed.

8 Claims, No Drawings

(56) References Cited

U.S. PATENT DOCUMENTS

| | | | |
|---|---|---|---|
| 11,389,458 | B2 | 7/2022 | Wang et al. |
| 11,690,849 | B2 | 7/2023 | Wang et al. |
| 11,744,833 | B2 | 9/2023 | Wang et al. |
| 2003/0229030 | A1 | 12/2003 | Theoharides |
| 2004/0006072 | A1* | 1/2004 | Franz .................. A61K 31/551 514/220 |
| 2005/0163843 | A1* | 7/2005 | Boehm ................ A61K 9/5084 424/468 |
| 2006/0051416 | A1 | 3/2006 | Rastogi et al. |
| 2009/0318703 | A1 | 12/2009 | Tani et al. |
| 2010/0152108 | A1 | 6/2010 | Hung et al. |
| 2012/0237570 | A1 | 9/2012 | Crain et al. |
| 2013/0252929 | A1 | 9/2013 | Lee et al. |
| 2014/0127328 | A1 | 5/2014 | Crain et al. |
| 2014/0158117 | A1 | 6/2014 | Dang et al. |
| 2015/0216849 | A1 | 8/2015 | Dedhiya et al. |
| 2016/0166543 | A1 | 6/2016 | Joshi et al. |
| 2017/0035780 | A1 | 2/2017 | Lulla et al. |
| 2018/0104294 | A1 | 4/2018 | Vuckovic |
| 2018/0116979 | A1 | 5/2018 | Clarence-Smith et al. |
| 2019/0030061 | A1 | 1/2019 | Rawas-Qalaji et al. |
| 2020/0323867 | A1 | 10/2020 | Wang et al. |
| 2020/0323868 | A1 | 10/2020 | Wang et al. |
| 2020/0323870 | A1 | 10/2020 | Wang et al. |
| 2020/0323871 | A1 | 10/2020 | Wang et al. |
| 2020/0323873 | A1 | 10/2020 | Wang et al. |
| 2020/0323877 | A1 | 10/2020 | Wang et al. |
| 2021/0069209 | A1 | 3/2021 | Wang et al. |
| 2022/0000882 | A1 | 1/2022 | Wang et al. |
| 2022/0096491 | A1 | 3/2022 | Wang et al. |
| 2022/0168318 | A1 | 6/2022 | Wang et al. |
| 2023/0000882 | A1 | 1/2023 | Wang et al. |
| 2023/0285408 | A1 | 9/2023 | Wang et al. |

FOREIGN PATENT DOCUMENTS

| | | |
|---|---|---|
| AU | 2019446955 A1 | 12/2021 |
| CA | 3136633 A1 | 10/2020 |
| CA | 3137393 A1 | 11/2020 |
| CA | 3139082 A1 | 11/2020 |
| CN | 113924098 A | 1/2022 |
| CN | 113939276 A | 1/2022 |
| CN | 114072945 A | 2/2022 |
| EP | 3952840 A1 | 2/2022 |
| EP | 3962488 A1 | 3/2022 |
| EP | 3973586 A1 | 3/2022 |
| EP | 4171539 A1 | 5/2023 |
| JP | 2010260808 A | 11/2010 |
| JP | 2012232978 A | 11/2012 |
| JP | 2016529307 A | 9/2016 |
| JP | 2019019113 A | 2/2019 |
| JP | 2022535644 A | 8/2022 |
| JP | 2022536017 A | 8/2022 |
| JP | 2022539944 A | 9/2022 |
| JP | 7365426 B2 | 10/2023 |
| WO | 02056876 A2 | 7/2002 |
| WO | 2006058022 A1 | 6/2006 |
| WO | 2007061454 A1 | 5/2007 |
| WO | 2014018563 A3 | 5/2014 |
| WO | 2020209872 A1 | 10/2020 |
| WO | 2020222799 A1 | 11/2020 |
| WO | 2020236159 A1 | 11/2020 |
| WO | 2021242235 A1 | 12/2021 |
| WO | 2021242297 A1 | 12/2021 |
| WO | 2021262196 A1 | 12/2021 |
| WO | 2023014361 A1 | 2/2023 |
| WO | 2023158424 A1 | 8/2023 |

OTHER PUBLICATIONS

Cummings et al. "Effect of Dextromethorphan-Quinidine on Agitation in Patients with Alzheimer Disease Dementia: A Randomized Clinical Trial". JAMA. 2015; 314(12):1242-1254. (Year: 2015).*

Ancill et al. "Agitation in the Demented Elderly: A Role for Benzodiazepines?", International Clinical Psychopharmacology. 1991; 6: 141-146. (Year: 1991).*

Starkstein et al. "The Construct of Generalized Anxiety Disorder in Alzheimer Disease". Am J Geriatr Psychiatry. Jan. 2007; 15(1):42-49. (Year: 2007).*

Munoz-Cano et al. "Severity of Allergic Rhinitis Impacts Sleep and Anxiety: Results from a Large Spanish Cohort". Clinical and Translational Allergy. 2018; 8 (Article 23), p. 1-9. (Year: 2018).*

Nader, Danilo and Gowing, Linda, 2020. Is Long-Term Benzodiazepine Use a Risk Factor for Cognitive Decline? Results of a Systematic Review. J Addiction. Jan. 23. doi: 10.1155/2020/1569456.

Riethmuller et al. Arzneimittel-Forschung, 1994, vol. 44, No. 10, pp. 1136-1140.

Sedeyn, Jonathan Histamine Induces Alzheimer's Disease-Like Blood Brain Barrier Breach and local cellular Responses in Mouse Brain Organotypic Culture. Hindawi. Aug. 21, 2015.

Simons, F.E., Simons, K.J. Clinical pharmacology of new histamine H1 receptor antagonist. Clin Pharmacokinet. 1999;36:329-352.

St-Jean, Genevieve; Turcotte, Isabelle; Bastien, Celyne H. Cerebral asymmetry in insomnia sufferers. Frontiers in Neurology 2012, 3, 1-12.

Szelenyi, I., Achterrath-Tuckermann, U., Schmidt, J., Minker, E., Paegelow, I., Werner, H. Azelastine: A multifaceted drug for asthma therapy. Agents Actions Suppl. 1991;34:295-311. (abstract).

Tanaka, Hibiki, Hashimoto, Mamoru, et al., 2015. Relationship Between Dementia Severity and Behavioural and Psychological Symptoms in Early-Onset Alzheimer's Disease. Psychogeriatrics. Dec. 2015; 15(4):242-7.

Verster, Joris C.; Volkerts, Edmund R.; 2004. Clinical Pharmacology, Clinical Efficacy, and Behavioral Toxicity of Alprazolam: A Review of the Literature. CNS Drug Reviews, vol. 10, No. 1, pp. 45-76.

Williams, Patricia B, Crandall, Elizabeth, and Sheppard, John D, 2010, Azelastine hydrochloride, a dual-acting anti-inflammatory ophthalmic solution, for treatment of allergic conjunctivitis. Clinical Ophthalmology 2010:4 993-1001.

Yoneda, Kazunori, et al. 1997, Suppression by Azelastine Hydrochloride of NF-KB Activation Involved in Generation of Cytokines and Nitric Oxide. Japanese Journal of Pharmacology, 73: 145-53.

Pacny, James P., Paice, Judith A., and Coalson, Dennis W., 2012. Separate and combined psychopharmacological effects of alprazolam and oxycodone in healthy volunteers, Aug. 1, 2012; 124(3): 274-282.

Co-Pending U.S. Appl. No. 16/382,885, Response to Jun. 5, 2020 Final office action filed Jul. 31, 2020, 9 pages.

U.S. Appl. No. 16/382,885, filed Apr. 12, 2019, Wang Jianmin.

(Wang, Jianmin) Co-Pending U.S. Appl. No. 16/382,885, filed Apr. 12, 2019, Specification and claims.

(Wang, Jianmin) Co-Pending U.S. Appl. No. 16/398,845, filed Apr. 30, 2019, Specification and Claims.

(Wang, Jianmin) Co-Pending U.S. Appl. No. 16/418,614, filed May 21, 2019, Specification and Claims.

(Wang, Jianmin) Co-pending U.S. Appl. No. 16/424,788, filed May 29, 2019, Specification and Claims.

(Wang, Jianmin) Co-Pending U.S. Appl. No. 16/426,121, filed May 30, 2019, Specification and Claims.

(Wang, Jianmin) Co-Pending U.S. Appl. No. 16/831,330, filed Mar. 26, 2020, Specification and Claims.

(Wang, Jianmin) Co-Pending U.S. Appl. No. 16/834,146, filed Mar. 30, 2020, Specification and Claims.

(Wang, Jianmin) Co-Pending U.S. Appl. No. 16/884,553, filed May 27, 2020, Specification and Claims.

(Wang, Jianmin) Co-Pending U.S. Appl. No. 16/913,927, filed Jun. 26, 2020, Specification and Claims.

(Wang, Jianmin) Co-Pending Application No. PCT/US19/29885, Filed Apr. 30, 2019, Specification and Claims.

(Wang, Jianmin) Co-Pending Application No. PCT/US19/33359, Filed May 21, 2019, Specification and Claims.

(Wang, Jianmin) Co-Pending Application No. PCT/US20/39916, Filed Jun. 26, 2020, Specification and Claims.

(Wang, Jianmin) Co-Pending Application No. PCT/US2019/027293, filed Apr. 12, 2019, Specification and Claims.

(56) References Cited

OTHER PUBLICATIONS

Bezprozvanny, Ilya. The rise and fall of Dimebon. National Institute of Health. Feb. 12, 2014.
Casale, T. B. The interaction of azelastine with human lung histamine H1, beta, and muscarinic receptor-binding sites. J Allergy Clin Immunol. 1989;83:771-776.
Category H1 receptor antagonists. Wikipedia. Sep. 20, 2012.
Chowdhury, Zahid Sadek et al., 2016, The Effect of Chronic Alprazolam Intake on Memory, Attention, and Psychomotor Performance in Healthy Human Male Volunteers. Behavioral Neurology, 2016, 9 pages, https://doi.org/10.1155/2016/3730940.
Ciprandi, G., Pronzato, C., Passalacqua, G., et al. Topical azelastine reduces eosinophil activation and Intercellular adhesion molecule-1 expression on nasal epithelial cells: An antiallergic activity. J Allergy Clin Immunol. 1996;98(6 Pt 1): 1088-1096.
Co-Pending U.S. Appl. No. 16/382,885, Final office action dated Jun. 5, 2020, 13 pgs.
Co-Pending U.S. Appl. No. 16/382,885, Non-Final office action and list of references dated Nov. 29, 2019, 23 pgs.
Co-Pending U.S. Appl. No. 16/382,885, Response to Nov. 29, 2019 Non-Final office action filed Mar. 2, 2020.
Co-Pending U.S. Appl. No. 16/382,885, Response to restriction requirement dated Oct. 2, 2019, 3pgs.
Co-Pending U.S. Appl. No. 16/382,885, Restriction Requirement dated Aug. 9, 2019, 7 pgs.
Co-Pending U.S. Appl. No. 16/398,845, Interview Summary dated Dec. 18, 2019, 7 pages.
Co-Pending U.S. Appl. No. 16/398,845, Non-Final Office Action dated Aug. 6, 2019, 25 pages.
Co-Pending U.S. Appl. No. 16/398,845, Notice of Allowance dated Jan. 21, 2020, 11 pages.
Co-Pending U.S. Appl. No. 16/398,845, Response to Non-Final Office Action dated Nov. 6, 2019, 9 pages.
Co-Pending U.S. Appl. No. 16/418,614, Interview Summary dated Dec. 18, 2019, 7 pages.
Co-Pending U.S. Appl. No. 16/418,614, Non-Final Office Action dated Aug. 6, 2019, 31 pages.
Co-Pending U.S. Appl. No. 16/418,614, Notice of Allowance dated Jan. 30, 2020, 12 pages.
Co-Pending U.S. Appl. No. 16/418,614, Response to Non-Final Office Action dated Nov. 6, 2019, 10 pages.
Co-pending U.S. Appl. No. 16/424,788 Non-Final Office Action, dated Nov. 29, 2019, 24 pgs.
Co-pending U.S. Appl. No. 16/424,788 Response to Nov. 29, 2019 Non-Final Office Action, filed Mar. 2, 2020.
Co-pending U.S. Appl. No. 16/424,788 Response to Restriction Requirement, dated Oct. 2, 2019, 3 pgs.
Co-pending U.S. Appl. No. 16/424,788 Restriction Requirement, dated Aug. 9, 2019, 7 pgs.
Co-Pending Application No. 16/426,121, Non-Final Office Action dated Aug. 6, 2019, 25 pages.
Co-Pending Application No. 16/426,121, Notice of allowance dated Jan. 21, 2020, 18 pages.
Co-Pending Application No. 16/426,121, Response to Non-Final Office Action dated Nov. 6, 2019, 9 pages.
Co-pending application No. PCT/US19/29885 International Search Report dated Jul. 15, 2019. 7 pages.
Co-pending application No. PCT/US19/33359 International Search Report and Written Opinion dated Aug. 15, 2019. 9 pages.
Co-Pending Application No. PCT/US2019/027293, Search Report & Written Opinion, dated Sep. 17, 2019, 8 pages.
Crowe, Simon F, Stranks, Elizabeth K, 2018. The Residual Medium and Long-term Cognitive Effects of Benzodiazepine Use: An Updated Meta-analysis. Arch Clin Neuropsychol. Nov. 1, 2018; 33 (7): 901-911.
Fawcett, J A; Kravitz, H M, 1982. Alprazolam: Pharmacokinetics, Clinical Efficacy, and Mechanism of Action. Pharmacotherapy, 2 (5): 243-54.
Goedert, M., Spillantini, M.G,. 2006. A century of Alzheimer's disease. Science, 314:777-81.
Hansen et al. Clinical Interventions in Aging 2008, vol. 3, No. 2, pp. 211-225.
Hatakeyama, AikO, Masahiko Fujii, Reiko Hatakeyama, Yumiko Fukuoka, Takuma Satoh-Nakagawa and Hidetada Sasaki, Azelastine hydrochloride on behavioral and psychological symptoms and activities of daily living in dementia patients, Geriatr Gerontol Int 2008; 8: 59-61 (2008).
Hazama, H., Nakajima, T., Hisada, T., Hamada, E., Omata, M., Kurachi, Y. Effects of azelastine on membrane currents in tracheal smooth muscle cells isolated from the guinea-pig. Eur J Pharmacol. 1994;259: 143-150.
Isbister, Geoffrey K., et al. 2004. Alprazolam is relatively more toxic than other benzodiazepines in overdose. British Journal of Clinical Pharmacology, vol. 58: 88-98.
Kempuraj, Duraisamy, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 Nov. 2003.
Naddafi, F., Mirshafiey A., The neglected role of histamine in Alzheimer's disease., Jun. 2013;28(4):327-36. doi: 10.1177/1533317513488925. Epub May 15, 2013.
(Wang, Jianmin) Co-Pending U.S. Appl. No. 17/094,405, filed Nov. 10, 2020, Specification and Claims.
(Wang, Jianmin) Co-Pending Application No. PCT/US20/34735, filed May 27, 2020, Specification and Claims.
(Wang, Jianmin) Co-Pending Application No. PCT/US20/59846, filed Nov. 10, 2020, Specification and figures.
Co-pending U.S. Appl. No. 16/424,788 Non-Final Office Action, dated Nov. 5, 2020, 8 pgs.
Co-pending U.S. Appl. No. 16/424,788, Final Office Action dated Aug. 28, 2020, 17 pages.
Co-pending U.S. Appl. No. 16/424,788, Response to Aug. 28, 2020 Final Office Action filed Oct. 19, 2020, 6 pages.
Co-Pending U.S. Appl. No. 16/426,121, Interview Summary dated Dec. 18, 2019, 7 pages.
Co-Pending U.S. Appl. No. 16/884,553, Non-Final Office Action dated Aug. 11, 2020, 26 pages.
Co-Pending U.S. Appl. No. 16/884,553, Response to Aug. 11, 2020 Non-Final Office Action dated Nov. 12, 2020, 8 pages.
Co-Pending U.S. Appl. No. 16/913,927, Non-Final Office Action dated Nov. 9, 2020, 24 pages.
Co-Pending U.S. Appl. No. 16/913,927, Response to Aug. 27, 2020 Restriction Requirement, filed Oct. 20, 2020, 5 pages.
Co-Pending U.S. Appl. No. 16/913,927, Restriction Requirement dated Aug. 27, 2020, 5 pages.
Co-Pending Application No. PCT/US20/34735, International Search Report and Written Opinion dated Aug. 17, 2020, 10 pages.
Co-Pending Application No. PCT/US20/39916, International Search Report and Written Opinion dated Oct. 8, 2020, 8 pages.
Co-Pending Application No. PCT/US2019/027293, Corrected Written Opinion, dated Oct. 29, 2019, 5 pages.
Galatowicz, G, Ajayi Y, Stern ME, Calder VL. Ocular antiallergic compounds selectively inhibit human mast cell cytokines in vitro and conjunctival cell infiltration in vivo. Clin Exp Allergy. 2007; 37:1648-1656.
Co-Pending U.S. Appl. No. 16/382,885, Non-Final office action dated Dec. 22, 2020, 19 pgs.
Co-Pending U.S. Appl. No. 16/382,885, Notice of Allowance dated Feb. 10, 2021, 9 pages.
Co-Pending U.S. Appl. No. 16/382,885, Response to Dec. 22, 2020 Non-Final office action filed Jan. 21, 2021, 7 pgs.
Co-pending U.S. Appl. No. 16/424,788 Corrected Notice of Allowance, dated Jan. 7, 2021, 5 pages.
Co-pending U.S. Appl. No. 16/424,788 Notice of Allowance, dated Dec. 17, 2020, 9 pages.
Co-pending U.S. Appl. No. 16/424,788 Response to Nov. 5, 2020 Non-Final Office Action, dated Dec. 2, 2020, 6 pages.
Co-Pending U.S. Appl. No. 16/884,553, Notice of Allowance dated Dec. 2, 2020, 9 pages.
Co-Pending U.S. Appl. No. 16/913,927, Non-Final Office Action dated Feb. 19, 2021, 19 pages.
Co-Pending U.S. Appl. No. 16/913,927, Response to Nov. 9, 2020 Non-Final Office Action filed Feb. 5, 2021, 8 pages.

(56) References Cited

OTHER PUBLICATIONS

Co-Pending U.S. Appl. No. 17/094,405, Restriction Requirement dated Jan. 26, 2021, 5 pages.
Troubat, Romain et al., Neuroinflammation and Depression: A Review. Eur J Neurosci. Mar. 9, 2020 DOI: 10.1111/ejn.14720.
(Wang, Jianmin) Co-Pending U.S. Appl. No. 17/394,898, filed Aug. 5, 2021, Specification and Claims.
(Wang, Jianmin) Co-Pending U.S. Appl. No. 17/459,868, filed Aug. 27, 2021, Specification and Claims.
(Wang, Jianmin) Co-Pending Application No. PCT/US21/44654, filed Aug. 5, 2021, Specification and Claims.
(Wang, Jianmin) Co-Pending Australia National Stage Application based on International Application No. PCT/US19/27293, Filed Nov. 5, 2021, Specification and Claims (See PCT/US19/27293).
(Wang, Jianmin) Co-Pending Canada National Stage Application based on International Application No. PCT/US19/29885, Filed Oct. 19, 2021, Specification and Claims (See PCT/US19/29885).
(Wang, Jianmin) Co-Pending Canada National Stage Application based on International Application No. PCT/US19/33359, Filed Nov. 3, 2021, Specification and Claims (See PCT/US19/33359).
(Wang, Jianmin) Co-Pending Canada National Stage Application No. 3,136,633, filed Oct. 8, 2021, Specification and Claims (see PCT/US19/27293).
(Wang, Jianmin) Co-Pending China National Stage Application based on International Application No. PCT/US19/29885, Filed Oct. 25, 2021, Specification and Claims (See PCT/US19/29885).
(Wang, Jianmin) Co-Pending China National Stage Application No. 201980095322.X, filed Oct. 11, 2021, Specification and Claims (see PCT/US19/27293).
(Wang, Jianmin) Co-Pending European National Stage Application No. 19924315.5, filed Nov. 11, 2021, Specification (See PCT/US19/27293) and Claims as filed (11 pages).
(Wang, Jianmin) Co-Pending Japan National Stage Application No. 2021-556914, filed Sep. 17, 2021, Specification and Claims (see PCT/US19/27293).
(Wang, Jianmin) Co-Pending Japan National Stage Application No. 2021-558496, filed Sep. 21, 2021, Specification and Claims (See PCT/US19/29885).
(Wang, Jianmin) Co-Pending Japan National Stage Application No. 2021-566489, filed Nov. 9, 2021, Specification and Claims (See PCT/US19/33359).
Bennett, F. C. and Molofsky, A. V., "The immune system and psychiatric disease: a basic science perspective", Clinical and Experimental Immunology, 197: 291-307.
Catena-Dell'osso, M. et al., 2011, Inflammatory and Neurodegenerative Pathways in Depression: A New Avenue for Antidepressant Development? Curr Med Chem. 18 (2), 245-55, Abstract, 2 pages.
Conti, Pio et al., "Impact of Mast Cells in Depression Disorder: Inhibitory Effect of IL-37 (New Frontiers)". Immunol Res, vol. 66 (3), 323-331 Jun. 2018.
Co-Pending U.S. Appl. No. 16/831,330, Non-Final Office Action dated Apr. 7, 2021, 16 bages.
Co-Pending U.S. Appl. No. 16/831,330, Notice of Allowance dated Aug. 3, 2021, 8 pages.
Co-Pending U.S. Appl. No. 16/831,330, Response to Apr. 7, 2021 Non-Final Office Action filed Jul. 21, 2021, 7 pages.
Co-Pending U.S. Appl. No. 16/834,146, Non-Final Office Action dated Nov. 15, 2021, 29 pages.
Co-Pending U.S. Appl. No. 16/913,927, Final Office Action dated Jun. 2, 2021, 16 pages.
Co-Pending U.S. Appl. No. 16/913,927, Non-Final Office Action dated Aug. 11, 2021, 17 pages.
Co-Pending U.S. Appl. No. 16/913,927, Response to Aug. 11, 2021 Non-Final Office Action, dated Nov. 10, 2021, 6 pages.
Co-Pending U.S. Appl. No. 16/913,927, Response to Feb. 19, 2021 Non-Final Office Action filed May 19, 2021, 10 pages.
Co-Pending U.S. Appl. No. 16/913,927, Response to Jun. 2, 2021 Final Office Action, dated Jul. 30, 2021, 6 pages.
Co-Pending U.S. Appl. No. 17/094,405, Final Office Action dated Jul. 30, 2021, 22 pages.
Co-Pending U.S. Appl. No. 17/094,405, Non-Final Office Action dated Apr. 14, 2021, 21 pages.
Co-Pending U.S. Appl. No. 17/094,405, Response to Apr. 14, 2021 Non-Final Office Action filed Jul. 14, 2021, 7 pages.
Co-Pending U.S. Appl. No. 17/094,405, Response to Jan. 26, 2021 Restriction Requirement, filed Apr. 5, 2021, 7 pages.
Co-Pending U.S. Appl. No. 17/094,405, Response to Jul. 30, 2021 Final Office Action, dated Sep. 30, 2021, 10 pages.
Co-Pending U.S. Appl. No. 17/394,898, Response to Oct. 21, 2021 Restriction Requirement, dated Nov. 10, 2021, 2 pages.
Co-Pending U.S. Appl. No. 17/394,898, Restriction Requirement dated Oct. 21, 2021, 9 pages.
Co-Pending U.S. Appl. No. 17/459,868, Preliminary Amendment, filed Aug. 27, 2021, 8 pages.
Co-Pending Application No. PCT/US20/59846, International Search Report and Written Opinion dated Mar. 8, 2021, 8 pages.
Co-Pending China National Stage Application based on International Application No. PCT/US19/29885, Application and amended claims as filed (26 pages) with English Translation of the Amended Claims (2 pages).
Co-Pending China National Stage Application No. 201980095322.X, English Version of Amended Claims as filed Oct. 11, 2021, 3 pages.
EHealthMe.com "Azelastine and Xanax drug interactions—a phase IV clinical study of FDA data", dated Jan. 7, 2021, 5 pages.
Georgin-Lavialle, S et al., "Mast Cells' Involvement in Inflammation Pathways Linked to Depression: Evidence in Mastocytosis." Mol Psychiatry. 21 (11), 1511-1516 Nov. 2016.
Guignet, Michelle et al., "Persistent behavior deficits, neuroinflammation, and oxidative stress in a rat model of acute organophosphate intoxication", vol. 133, Jan. 2020, 101131.
Horak, Friedrich, "Effectiveness of twice daily azelastine nasal spray in patients with seasonal allergic rhinitis," Ther. Clin. Risk Manag., Oct. 2008; 4(5): 1009-1022.
Hou, Ruihua and Baldwin, David S., "A neuroimmunological perspective on anxiety disorders", Human Psychopharmacol Clin Exp. 2012, vol. 27: 6-14.
Hou, Ruihua et al., "Peripheral inflammatory cytokines and immune balance in Generalized Anxiety Disorder: case-controlled study", Brain Behav Immun. May 2017; 62: 212-218.
Jeon, Sang Won and Kim, Yong Ku, "Detrimental effect of preservative in eye drops: Neuroinflammation and cytokine abnormality in major depression: Cause or consequence in that illness?" World Journal of Psychiatry, Sep. 22, 2016; 6(3): 283-293.
Kappelmann, N. et al., "Antidepressant activity of anti-cytokine treatment: a systematic review and meta-analysis of clinical trials of chronic inflammatory conditions", Molecular Psychiatry, 2018, vol. 23, 335-313.
Kohler, Ole et al., "Inflammation in Depression and the Potential for Anti-Inflammatory Treatment." Current Neuropharmacology, 2016, 11, 732-712.
Koo, Ja Wook et al., 2010, Nuclear factor-κB is a critical mediator of stress impaired neurogenesis and depressive behavior. PNAS, Feb. 9, 2010, vol. 107 (6) 2669-2674.
Liu, Chun-Hong et al., Role of inflammation in depression relapse, Journal of Neuroinflammation (2019) 16:90, 11 pages.
Maeng, Sung Ho and Hong, Heeok, "Inflammation as the Potential Basis in Depression." Int Neurourol J 2019; vol. 23(Suppl 2): S63-71.
Niazi, Sarfaraz K., Handbook of Pharmaceutical Manufacturing Formulations vols. 1-6, 2004, 304 pages.
Niraula, Anzela et al., "IL-6 Induced by Social Stress Promotes a Unique Transcriptional Signature in the Monocytes That Facilitate Anxiety." Biol Psychiatry 85 (8), 679-689, Apr. 15, 2019.
(Wang, Jianmin) Co-Pending U.S. Appl. No. 17/546,342, filed Dec. 9, 2021, Specification and Claims.
(Wang, Jianmin) Co-Pending Application No. 17/673,136, filed Feb. 16, 2022, Specification and Claims.
(Wang, Jianmin) Co-Pending Application No. PCT/US22/16545, filed Feb. 16, 2022, Specification and Claims.
(Wang, Jianmin) Co-Pending Australia National Stage Application No. 2019443520, Effective Filing Date Apr. 30, 2019, Specification

(56) References Cited

OTHER PUBLICATIONS and Claims (See PCT/US19/29885, which published as WO 2020/222799, for Specification and Claims as filed).
(Wang, Jianmin) Co-Pending Australia National Stage Application No. 2019445048, Effective Filing Date Apr. 12, 2019, Specification and Claims (See PCT/US19/27293, which published as WO 2020/209872, for Specification and Claims as filed).
(Wang, Jianmin) Co-Pending Australia National Stage Application No. 2019446955, Effective Filing Date May 21, 2019, Specification and Claims (See PCT/US19/33359, which published as WO2020/236159, for Specification and Claims as filed).
(Wang, Jianmin) Co-Pending Canada National Stage Application No. 3,136,633, filed Oct. 8, 2021, Specification and Claims, 25 pages.
(Wang, Jianmin) Co-Pending Canada National Stage Application No. 3,137,393, Filed Oct. 19, 2021, Specification and Claims, 17 pages.
(Wang, Jianmin) Co-Pending Canada National Stage Application No. 3,139,082, Filed Nov. 3, 2021, Claims and Amended Specification, 25 pages.
(Wang, Jianmin) Co-Pending China National Stage Application No. 201980095322.X, filed Oct. 11, 2021, Specification and Claims (32 pages) (see PCT/US19/27293, which published as WO2020/209872 for English Translation).
(Wang, Jianmin) Co-Pending China National Stage Application No. 201980095741.3, Filed Oct. 25, 2021, Specification and Amended Claims as filed (26 pages) with English Translation of the Amended Claims (2 pages) (See PCT/US19/29885, which published as WO 2020/222799, for English Translation of the Specification).
(Wang, Jianmin) Co-Pending China National Stage Application No. 201980096574.4, Filed Nov. 18, 2021, Specification and Amended Claims as filed (48 pages) with English Translation of the Amended Claims (4 pages) (See PCT/US19/33359, which published as WO2020/236159, for English Translation of the Specification).
(Wang, Jianmin) Co-Pending European National Stage Application No. 19924315.5, filed Nov. 11, 2021, Specification and Amended Claims as filed (34 pages).
(Wang, Jianmin) Co-Pending European National Stage Application No. 19927207.1, filed Nov. 29, 2021, Specification and Amended Claims as filed (26 pages).
(Wang, Jianmin) Co-Pending European National Stage Application No. 19929933.0, filed Dec. 21, 2021, Specification and Amended Claims as filed (35 pages).
(Wang, Jianmin) Co-Pending Japan National Stage Application No. 2021-556914, filed Sep. 17, 2021, Specification and Claims (19 pages) (see PCT/US19/27293, which published as WO 2020/209872, for English Translation).
(Wang, Jianmin) Co-Pending Japan National Stage Application No. 2021-558496, filed Sep. 21, 2021, Specification and Claims (15 pages) (See PCT/US19/29885, which published as WO 2020/222799, for English Translation).
(Wang, Jianmin) Co-Pending Japan National Stage Application No. 2021-566489, filed Nov. 9, 2021, Request for Entry and Specification and Claims (18 pages) (See PCT/US19/33359, which published as WO2020/236159, for English Translation of Specification and Claims).
Co-Pending U.S. Appl. No. 16/834,146, Response to Nov. 15, 2021 Non-Final Office Action, dated Feb. 22, 2022, 9 pages.
Co-Pending U.S. Appl. No. 16/913,927, Final Office Action dated Dec. 3, 2021, 12 pages.
Co-Pending U.S. Appl. No. 17/394,898, Non-Final Office Action dated Nov. 24, 2021, 9 pages.
Co-Pending U.S. Appl. No. 17/394,898, Response to Nov. 24, 2021 Non-Final Office Action, dated Feb. 23, 2022, 9 pages.
Co-Pending Application No. PCT/US21/44654, International Search Report and Written Opinion, dated Nov. 15, 2021, 10 pages.
Hua, S. "Advances in Nanoparticulate Drug Delivery Approaches for Sublingual and Buccal Administration". Nov. 10, 2019 (Article 1328), pp. 1-9.
(Wang, Jianmin) Co-Pending U.S. Appl. No. 17/940,533, filed Sep. 8, 2022, Specification and Claims.
Bartlett, D. and Bear, M., "Rhinorrhea as a Result of Alzheimer's Disease Treatment: A Case Report", The Senior Care Pharmacist. Dec. 2019; 34(10):669-673, 5 pages.
Co-Pending Application No. 16/834,146, Final Office Action dated Mar. 18, 2022, 20 pages.
Co-Pending U.S. Appl. No. 16/834,146, Notice of Allowance dated Jun. 6, 2022, 8 pages.
Co-Pending U.S. Appl. No. 16/834,146, Response to Mar. 18, 2022 Final Office Action, dated May 12, 2022, 7 pages.
Co-Pending U.S. Appl. No. 16/913,927, Notice of Allowance dated Mar. 21, 2022, 11 pages.
Co-Pending U.S. Appl. No. 16/913,927, Response to Dec. 3, 2021 Final Office Action, dated Mar. 3, 2022, 3 pages.
Co-Pending U.S. Appl. No. 17/094,405, Non-Final Office Action dated Apr. 14, 2022, 38 pages.
Co-Pending U.S. Appl. No. 17/394,898, Examiner-Initiated Interview Summary for Interview conducted Mar. 4, 2022, 1 page.
Co-Pending U.S. Appl. No. 17/394,898, Notice of Allowance and Examiner's Amendment dated Mar. 17, 2022, 13 pages.
Co-Pending U.S. Appl. No. 17/673,136, Non-Final Office Action dated Jul. 22, 2022, 20 pages.
Co-Pending U.S. Appl. No. 17/673,136, Response to May 3, 2022 Restriction Requirement, dated Jun. 9, 2022, 2 pages.
Co-Pending U.S. Appl. No. 17/673,136, Restriction Requirement dated May 3, 2022, 5 pages.
Co-Pending U.S. Appl. No. 17/940,533, Preliminary Amendment dated Sep. 8, 2022, 10 pages.
Co-Pending Application No. PCT/US22/16545, International Search Report and Written Opinion dated Jul. 7, 2022, 11 pages.
Co-Pending Application No. PCT/US22/16545, Invitation to Pay Fees dated Apr. 19, 2022, 2 bages.
Co-Pending European National Stage Application No. 19924315.5, Extended European Search Report dated Oct. 24, 2022, 6 pages.
Co-Pending Japan National Stage Application No. 2021-556914 Voluntary Amendment and Request for Exam dated Apr. 11, 2022, JP version (5 pages) and English (3 pages).
Co-Pending Japan National Stage Application No. 2021-558496 Voluntary Amendment and Request for Exam dated Apr. 14, 2022, JP version (4 pgs) and English (2 pgs).
Co-Pending Japan National Stage Application No. 2021-566489 Voluntary Amendment and Request for Exam dated May 17, 2022, JP version (5 pgs) and English (4 pgs).
Lv, Wei-jie et al., "Melatonin Alleviates Neuroinflammation and Metabolic Disorder in DSS-Induced Depression Rats". Oxidative Medicine and Cellular Longevity 2020, Article ID 1241894, 17 pages.
Patki, G. and Y.S. Lau, "Melatonin protects against neurobehavioral and mitochondrial deficits in a chronic mouse model of Parkinson's disease". Pharmacol. Biochem. Behav. 2011, 99: 704-711, 20 pages.
Tariot, P. N. et al. Memantine Treatment in Patients With Moderate to Severe Alzheimer Disease Already Receiving Donepezil, JAMA, Jan. 21, 2004, vol. 291, No. 3, p. 317-324, 8 pages.
"Donepezil—Medline Plus", Medline Plus, Dec. 15, 2017, 6 pages, [retrieved Dec. 19, 2022], https://medlineplus.gov/druginfo/meds/a697032.html.
"EPAR summary for the public", European Medicines Agency, Dec. 1, 2012, 3 pages, [retrieved Dec. 19, 2022], https://www.ema.europa.eu/en/documents/overview/prometax-epar-summary-public_en.pdf.
"Razadyne-galantamine hydrobromide tablet, film coated Rebel Distributors Corp", Dailymed, Nov. 11, 2010, 32 pages, [retrieved Dec. 19, 2022], https://dailymed.nlm.nih.gov/dailymed/drugInfo.cfm?setid=e62efb5a-d2cc-4e11-9e61-10e65ef3d897.
(Wang, Jianmin) Co-Pending U.S. Appl. No. 18/318,804, filed May 17, 2023, Specification and Claims.
(Wang, Jianmin) Co-Pending Canada National Stage Application No. 3,183,560, Filed Dec. 20, 2022, Claims and Specification (See WO2021/262196).
(Wang, Jianmin) Co-Pending China National Stage Application No. 202080102343.2, Filed Dec. 22, 2022, Specification and Amended

(56) References Cited

OTHER PUBLICATIONS

Claims as filed (28 pages) with English Translation of the Amended Claims (3 pages) (See WO2021/262196, for English Translation of the Specification).
(Wang, Jianmin) Co-Pending European National Stage Application No. 20942038.9, filed Jan. 25, 2023, Specification and Amended Claims as filed (23 pages).
(Wang, Jianmin) Co-Pending Japan National Stage Application No. 2022-578962, filed Dec. 21, 2022, Specification and Claims (See WO2021/262196).
Beitz, Janice M. "Parkinson's disease: a review", Frontiers in Bioscience S6, 65-74, Jan. 1, 2014, 10 pages.
Co-Pending U.S. Appl. No. 17/459,868, Non-Final Office Action dated Mar. 10, 2023, 18 pages.
Co-Pending U.S. Appl. No. 17/459,868, Response to Mar. 10, 2023 Non-Final Office Action, dated Mar. 22, 2023, 3 pages.
Co-Pending Application No. 17/673,136, Applicant-Initiated Interview Summary dated Apr. 7, 2023, 2 pages.
Co-Pending Application No. 17/673,136, Applicant-Initiated Interview Summary dated May 1, 2023, 5 pages.
Co-Pending Application No. 17/673,136, Final Office Action dated Feb. 7, 2023, 13 pages.
Co-Pending Application No. 17/673,136, Non-Final Office Action dated Apr. 4, 2023, 11 pages.
Co-Pending Application No. 17/673,136, Notice of Allowance dated Jun. 7, 2023, 8 pages.
Co-Pending Application No. 17/673,136, Response to Apr. 4, 2023 Non-Final Office Action, dated May 2, 2023, 6 pages.
Co-Pending U.S. Appl. No. 17/673,136, Response to Feb. 7, 2023 Final Office Action, dated Feb. 21, 2023, 7 pages.
Co-Pending Application No. 17/673,136, Response to Jul. 22, 2022 Non-Final Office Action, dated Dec. 22, 2022, 8 pages.
Co-Pending U.S. Appl. No. 17/940,533, Non-Final Office Action dated Mar. 9, 2023, 21 pages.
Co-Pending U.S. Appl. No. 17/940,533, Response to Jan. 9, 2023 Restriction Requirement, dated Jan. 24, 2023, 2 pages.
Co-Pending U.S. Appl. No. 17/940,533, Response to Mar. 9, 2023 Non-Final Office Action, dated Jun. 9, 2023, 8 pages.
Co-Pending U.S. Appl. No. 17/940,533, Restriction Requirement dated Jan. 9, 2023, 5 pages.
Co-Pending China National Stage Application No. 201980095322.X, First Office Action (7 pages) dated Jan. 19, 2023 and English Translation (7 pages).
Co-Pending China National Stage Application No. 201980095322.X, Response to Jan. 19, 2023 Office Action dated May 30, 2023 (7 pages) and English Translation of the amended claims (4 pages).
Co-Pending China National Stage Application No. 201980095741.3, Office Action dated Mar. 23, 2023 (8 pages) and English Translation (9 pages).
Co-Pending European National Stage Application No. 19924315.5, Response to Extended European Search Report, dated May 19, 2023, 6 pages.
Co-Pending European National Stage Application No. 19927207.1, Extended European Search Report dated Nov. 10, 2022, 10 pages.
Co-Pending European National Stage Application No. 19927207.1, Response to Nov. 10, 2022 Extended European Search Report, dated Jun. 9, 2023, 11 pages.
Co-Pending European National Stage Application No. 19929933.0, Extended European Search Report dated Dec. 14, 2022, 11 pages.
Co-Pending Japan National Stage Application No. 2021-556914 Office Action dated Feb. 24, 2023 (4 pages) and English Translation (5 pages).
Co-Pending Japan National Stage Application No. 2021-556914 Voluntary Amendment and Request for Exam dated Apr. 11, 2022, JP version (5 pages) and English translation of the amended claims (4 pages).
Co-Pending Japan National Stage Application No. 2021-558496, Office Action dated Feb. 24, 2023 (3 pages) and English Translation (4 pages).
Co-Pending Japan National Stage Application No. 2021-566489, Office Action dated Mar. 29, 2023 (5 pages) and English Translation (7 pages).
Co-Pending Japan National Stage Application No. 2022-578962, Voluntary Amendment dated Feb. 24, 2023 (3 pages) with English Translation of the Amended Claims (3 pages).
Frisch, C. et al. "The histamine H1-antagonist chlorpheniramine facilitates learning in aged rats", Neuroscience Letters, vol. 229, No. 2, Jun. 27, 1997, pp. 89-92.
Girard, J. et al. "Azelastine protects against CA1 traumatic neuronal injury in the hippocampal slice", European Journal of Pharmacology, vol. 300, Jan. 1, 1996, pp. 43-49.
Ljubenkov, Peter et al. "Dementia", Seminars in Neurology, 2016, vol. 36, No. 4, pp. 397-404.
Singh, Tanvir et al. "Alprazolam as a monotherapy for anxiety and depression", Psychiatry (Edgmont). Nov. 2005; 2(11):32, 1 page.
Sors, A. et al., "The Synergistic Enhancing-Memory Effect of Donepezil and S 38093 (a Histamine H3 Antagonist) Is Mediated by Increased Neural Activity in the Septo-hippocampal Circuitry in Middle-Aged Mice", Frontiers in Pharmacology, 2016, vol. 7, No. 492, pp. 1-12.
Co-Pending China National Stage Application No. 201980095322.X, Second Office Action dated Jul. 8, 2023, 5 pages.
Co-Pending U.S. Appl. No. 17/940,533, Final Office Action dated Jul. 27, 2023, 11 pages.
Co-Pending U.S. Appl. No. 17/940,533, Response to Jul. 27, 2023 Final Office Action, dated Oct. 27, 2023, 12 pages.
Co-Pending China National Stage Application No. 201980095322.X, English Translation of the Second Office Action dated Jul. 8, 2023, 8 pages.
Co-Pending European National Stage Application No. 19929933.0, Response to Extended European Search Report, filed Jul. 20, 2023, 17 pages.
Co-Pending European National Stage Application No. 20942038.9, Extended European Search Report dated Dec. 20, 2023, 9 pages.
Jones, Roy W. "Dimebon disappointment", Alzheimer's Research & Therapy 2010, 2:25, 3 pages.
Spector, Sheldon L. et al. "Pharmacodynamic evaluation of azelastine in subjects with asthma", J. Allergy Clin. Immunol., Jul. 1987, 75-80.
Co-Pending China National Stage Application No. 201980095322.X, Response to Second Office Action dated Jan. 17, 2024 (7 pages) and English Translation of the Amended Claims (4 pages).

\* cited by examiner

PHARMACEUTICAL COMPOSITIONS AND METHODS FOR ANXIETY, DEPRESSION AND OTHER PSYCHIATRIC DISORDERS

CROSS-REFERENCE TO RELATED APPLICATIONS

The present application is a Continuation in Part application of U.S. patent application Ser. No. 16/382,885 filed on Apr. 12, 2019, the disclosure of which is hereby incorporated by reference herein in its entirety.

FIELD OF THE INVENTION

The invention relates to the field of practical medicine, namely, to the use of pharmaceutical compositions for treating, preventing and/or alleviating manifestations of one or more psychiatric disorders, such as major depressive disorder, generalized anxiety disorder, panic disorder, agitation, social anxiety disorder, mild chronic depression, obsessive-compulsive disorder, premenstrual dysphoric disorder, seasonal affective disorder, dysthymia, childhood enuresis, bipolar disorder, posttraumatic stress disorder and sleep disorder related to anxiety.

BACKGROUND OF THE INVENTION

Psychiatric disorders, including anxiety, depression, panic disorder, agitation, affect more than one in ten people globally (10.7%) as reported by the Institute for Health Metrics and Evaluation in their flagship Global Burden of Disease study in 2017. Two examples of psychiatric disorders, major depressive disorders (MDDs) and generalized anxiety disorder (GAD), are common, severe, chronic and often life-threatening illnesses. More than 20% of the adult population suffers from these conditions at some time during their life. Suicide is estimated to be a cause of death in up to approximately 15% of individuals with MDDs. In addition, MDDs represent a major risk factor for the development of cardiovascular disease and death after myocardial infarction.

Treatments for anxiety, depression and the like include selective serotonin reuptake inhibitors (SSRIs), such as citalopram (Celexa), escitalopram oxalate (Lexapro), fluoxetine (Prozac), fluvoxamine (Luvox), paroxetine HRI (Paxil), and sertraline (Zoloft); selective serotonin & norepinephrine inhibitors (SNRIs), such as desvenlafaxine (Khedezla), desvenlafaxine succinate (Pristiq), duloxetine (Cymbalta), levomilnacipran (Fetzima), and venlafaxine (Effexor); tetracyclic antidepressants of noradrenergic and specific serotonergic antidepressants (NaSSAs), such as Remeron; tricyclic antidepressants, such as Elavil, imipramine (Tofranil), nortriptyline (Pamelor), and Sinequan; monoamine oxidase inhibitors (MAOIs), such as isocarboxazid (Marplan), phenelzine (Nardil), selegiline (EMSAM), and tranylcypromine (Parnate); and benzodiazepines, such as alprazolam (Xanax), diazepam (Valium), buspirone (Buspar), and lorazepam (Ativan). These drugs do carry a risk of addiction, tolerance, loss of effectiveness, inciting violent or self-destructive actions, fatigue, and drowsiness along with nausea, increased appetite and weight gain, loss of sexual desire and other sexual problems, insomnia, dry mouth, blurred vision, and so on.

Clinically, new treatments are highly and urgently needed that have tremendous improvement and significant impact to the management of patients with psychiatric disorders, such as treatments being highly effective and with much less adverse effects.

Treatments of psychiatric disorders based on pharmacological mechanisms of action of SSRI, SNRI, NaSSA and MAOI have shown their limitations. Increasing evidence indicates that inflammatory processes can cause and contribute to the development of psychiatric disorders.

Inflammation can be defined as one of the immune responses for protecting living organisms from damage. The immune system can be triggered by various factors such as pathogens, damage to cells and stress that may induce acute or chronic inflammatory responses in organs including the brain, potentially leading to tissue damage or disease. The latest advancements in neurobiological research provides increasing evidence that inflammatory and neurodegenerative pathways play a relevant role in depression and anxiety. Preclinical and clinical studies on depression and anxiety highlighted an increased production of inflammatory markers, such as interleukin (IL)-1, IL-6, tumor necrosis factor (TNF)-$\alpha$ and interferon (INF)-$\alpha$ and $\gamma$, and overactivated inflammatory signaling pathways including nuclear factor kappa B (NF-$\kappa$B). Other studies show that acute and chronic administration of cytokines or cytokine inducers were found to trigger depressive and/or anxiety symptoms. According to the cytokine hypothesis, depression and anxiety would be due to a stress-related increased production of pro-inflammatory cytokines that, in turn, would lead to increased oxidative and nitrosative brain damage and consequent reduced availability of tryptophan and serotonin (5-HT). Cytokines would also play a role in the onset of the glucocorticoid resistance, underlying the overdrive of the hypothalamic-pituitary-adrenal axis. Therefore, activation of the inflammatory and neurodegenerative pathways would lead to the brain damage observed in depression and/or anxiety through both reduced neurogenesis and increased neurodegeneration.

Azelastine is classified pharmacologically as a second-generation antihistamine and is a relatively selective, non-sedative, competitive antagonist at $H_1$ receptors for treatment of allergic rhinitis and asthma. But, more uniquely, its inhibition of inflammatory mediators and its mast cell stabilizing effects, in addition to its antihistaminic activity, place it among the new generation of dual-acting anti-inflammatory drugs. Its ability to modify several other mediators of inflammation, such as IL-1, IL-6, TNF-$\alpha$ and INF-$\alpha$, and to reduce overactivation of NF-$\kappa$B inflammatory signaling pathway might contribute to its mechanism of action of potential treatment of psychiatric disorders, such as anxiety, depression, panic disorder, agitation, bipolar disorder (BD), premenstrual dysphoric disorder (PDD). In vitro and in vivo studies, as well as clinical trials support the dual effects of direct inhibition and stabilization of inflammatory cells. In vitro data indicate that azelastine's affinity for inhibition of mast cell degranulation may also decrease the release of other inflammatory mediators, including leukotrienes and interleukin-1$\beta$, among others. Preclinical studies show that azelastine also directly antagonizes other mediators of inflammation, such as tumor necrosis factor-$\alpha$, leukotrienes, endothelin-1, and platelet-activating factor.

Alprazolam, the 19th most prescribed drug with 27 million prescriptions in the United States in 2019, is a benzodiazepine derivative that is currently used in the treatment of generalized anxiety, panic attacks, and depression. Alprazolam binds non-selectively to the gamma-amino butyric acid A (GABAA)-benzodiazepine receptor complex. At the receptor complex, alprazolam facilitates the binding of GABA and increases the influx of chloride ions. The presence of GABA, in turn, inhibits the action of several connected brain structures, resulting in a general slowing of brain activity. Further, the activated GABA system interacts with other neurotransmitter systems, including noradrenergic, serotonergic, cholinergic, and opioidergic systems. Alprazolam's interactions with the serotonergic and noradrenergic pathways to the limbic system and brain stem structures (e.g., locus coeruleus) contribute to its clinical effectiveness in the treatment of anxiety and depression. Alprazolam has a fast onset of symptom relief and is significantly superior to placebo. But its adverse effects, such as cognitive and psychomotor effects, drowsiness, sedation, withdrawal and rebound effects limit its therapeutic applications. One of the most critical adverse effects of alprazolam is to impair performance in a variety of skills in patients due to its effect on psychomotor and memory functioning.

Therefore, a unique combination of azelastine (antihistamine agent with anti-inflammatory activities) with alprazolam (GABA-benzodiazepine receptor complex agonist) would potentially be, in terms of working through multi-mechanisms of actions, effective treatments for psychiatric disorders.

SUMMARY OF THE INVENTION

The present invention includes a pharmaceutical composition that comprises two active pharmaceutical ingredients. This pharmaceutical composition comprises the first active ingredient that is azelastine or a pharmaceutically acceptable salt of azelastine and the second active ingredient that is alprazolam.

In some embodiments of this invention, the pharmaceutically acceptable salt of azelastine in the pharmaceutical composition is azelastine hydrochloride and/or any one or more salt of azelastine such as those disclosed in U.S. Pat. Nos. 6,017,909, 5,086,050 and/or 5,068,233.

In some embodiments of this invention, azelastine hydrochloride (and/or other salt thereof) in the pharmaceutical composition is provided in an amount of about 1 mg to about 8 mg and alprazolam in an amount of about 0.2 mg to about 4 mg.

The present invention also includes an oral pharmaceutical dosage form of the pharmaceutical composition that is a solid, liquid, gel, or solution form.

The present invention further includes use of the composition, such as by oral dosage, through administration to patients with psychiatric disorders, such as one or more of major depressive disorder (MDD), generalized anxiety disorder (GAD), panic disorder, agitation, social anxiety disorder (SAD), mild chronic depression (MCD), obsessive-compulsive disorder (OCD), premenstrual dysphoric disorder (PDD), seasonal affective disorder (SAD), dysthymia, childhood enuresis, bipolar disorder, posttraumatic stress disorder (PSD) and sleep disorders related to anxiety (SDRA).

In some embodiments of this invention, an oral pharmaceutical dosage form of the pharmaceutical composition containing azelastine hydrochloride (and/or other salt thereof) in an amount of about 1 mg to about 8 mg and alprazolam in an amount of about 0.2 mg to about 4 mg is administered to patients with any one or more psychiatric disorder, such as MDD, GAD, panic disorder, agitation, SAD, MCD, OCD, PDD, SAD, dysthymia, childhood enuresis, bipolar disorder, PSD, SDRA.

Embodiments include Aspect 1, which are pharmaceutical compositions comprising: azelastine or a pharmaceutically acceptable salt of azelastine; alprazolam; and one or more pharmaceutically acceptable excipients.

Aspect 2 is the pharmaceutical composition of Aspect 1, wherein the azelastine or the pharmaceutically acceptable salt of azelastine is present in the pharmaceutical composition in an amount in the range of about 1 mg to about 8 mg.

Aspect 3 is the pharmaceutical composition of Aspect 1 or 2, wherein the alprazolam is present in the pharmaceutical composition in an amount in the range of about 0.2 mg to about 4 mg.

Aspect 4 is the pharmaceutical composition of any of Aspects 1-3, wherein the alprazolam is present in the pharmaceutical composition in an amount in the range of about 0.2 mg to about 4 mg.

Aspect 5 is the pharmaceutical composition of any of Aspects 1-4, wherein: the azelastine or the pharmaceutically acceptable salt of azelastine is present in the pharmaceutical composition in an amount in the range of about 1 mg to about 6 mg; and the alprazolam is present in the pharmaceutical composition in an amount in the range of about 0.2 mg to about 1 mg.

Aspect 6 is the pharmaceutical composition of any of Aspects 1-5, wherein the pharmaceutically acceptable salt of azelastine is azelastine hydrochloride.

Aspect 7 is the pharmaceutical composition of any of Aspects 1-6, wherein the pharmaceutically acceptable salt of azelastine is azelastine hydrochloride and is present in an amount in the range of up to about 8 mg.

Aspect 8 is the pharmaceutical composition of any of Aspects 1-7, wherein the azelastine hydrochloride is present in an amount in the range of about 1 mg to about 6 mg.

Aspect 9 is the pharmaceutical composition of any of Aspects 1-8, wherein the pharmaceutical composition is formulated as an oral pharmaceutical dosage form.

Aspect 10 is the pharmaceutical composition of any of Aspects 1-9, wherein the oral pharmaceutical dosage form is a solid form or a liquid form.

Aspect 11 is a method comprising: administering a pharmaceutical composition to a patient; wherein the pharmaceutical composition comprises effective amounts of azelastine or a pharmaceutically acceptable salt of azelastine and alprazolam; and wherein the effective amounts together are sufficient to treat one or more symptoms of one or more psychiatric disorder of the patient.

Aspect 12 is the method of Aspect 11, wherein one or more of the psychiatric disorders are selected from major depressive disorders, generalized anxiety disorder, panic disorder, agitation, social anxiety disorder, mild chronic depression, premenstrual dysphoric disorder, anxiety-related sleep disorder.

Aspect 13 is the method of Aspect 11 or 12, wherein the pharmaceutical composition is administered once or twice a day, or once every 2 or 3 or 4 days to the patient in an oral solid or liquid form.

Aspect 14 is the method of any of Aspects 11-13, wherein the pharmaceutical composition is administered for a period of at least 6 weeks.

Aspect 15 is the method of any of Aspects 11-14, wherein the azelastine or the pharmaceutically acceptable salt of azelastine is present in the pharmaceutical composition in an amount in the range of about 1 mg to about 8 mg.

Aspect 16 is the method of any of Aspects 11-15, wherein the alprazolam is present in the pharmaceutical composition in an amount in the range of about 0.2 mg to about 4 mg.

Aspect 17 is the method of any of Aspects 11-16, wherein the alprazolam is present in the pharmaceutical composition in an amount in the range of about 0.2 mg to about 4 mg.

Aspect 18 is the method of any of Aspects 11-17, wherein the azelastine or the pharmaceutically acceptable salt of azelastine is present in the pharmaceutical composition in an amount in the range of about 1 mg to about 8 mg.

Aspect 19 is the method of any of Aspects 11-18, wherein: the azelastine or the pharmaceutically acceptable salt of azelastine is present in the pharmaceutical composition in an amount in the range of about 1 mg to about 8 mg; and the alprazolam is present in the pharmaceutical composition in an amount in the range of about 0.2 mg to about 4 mg.

DETAILED DESCRIPTION OF THE INVENTION

Through clinical practice, the inventors of the present invention found that a pharmaceutical composition with oral dosage forms comprising the active agents, a salt form of azelastine and alprazolam, is suitable for treating patients suffering from psychiatric disorders such as one or more of major depressive disorder (MDD), generalized anxiety disorder (GAD), panic disorder, agitation, and sleep disorders related to anxiety (SDRA).

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

Psychiatric disorders can include but are not limited to MDD, GAD, panic disorder, agitation, SAD, MCD, OCD, PDD, SAD, dysthymia, childhood enuresis, bipolar disorder, PSD, SDRA.

As used herein, the term "alprazolam" refers to alprazolam free base, 8-Chloro-1-methyl-6-phenyl-4H-s-triazolo(4,3-a)(1,4)benzodiazepine.

As used herein, the term "azelastine" refers to azelastine free base, or 4-(p-Chlorobenzyl)-2-(hexahydro-1-methyl-1H-azepin-4-yl)-1-(2H)-phthalazinone. In certain embodiments, azelastine also includes any pharmaceutically acceptable salt, such as the hydrochloride or HCl salt. Preferably, in any embodiments of the invention as described herein, azelastine is in the form of its hydrochloride salt, as azelastine hydrochloride or azelastine HCl. More preferably, in any embodiment of the invention as described herein, reference to the amounts and dosage ranges of azelastine in the solid oral dosage forms are to the amounts and dosage ranges of azelastine hydrochloride.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to affect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by oral administration. Administration may be by way of any one or more of capsule, tablet, gel, spray, drops, solution, suspensions, syrups, or the like.

The term "about" used herein in the context of quantitative measurements means the indicated amount±10%. For example, with a ±10% range, "about 2 mg" can mean 1.8-2.2 mg.

The pharmaceutical compositions may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration, for example, admixed with any one or more of conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects sustained release formulations may even be preferred. Capsules may be formulated by mixing the pharmaceutical composition with a pharmaceutical diluent which is inert and inserting this mixture into a hard gelatin capsule having the appropriate size. If soft capsules are desired, a slurry of the pharmaceutical composition with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or other non-nutritive sweetener, and/or a biological sweetener and/or a flavoring agent, such as in the form of an elixir.

The solid oral dosage formulation of this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutical compositions provided in accordance with the present disclosure can be typically administered orally. This disclosure therefore provides pharmaceutical compositions that comprise a solid dispersion comprising azelastine and alprazolam as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutical compositions may further comprise pharmaceutical excipients such as diluents, binders, fillers, glidants, disintegrants, lubricants, solubilizers, and combinations thereof. Some examples of suitable excipients are described herein. When the pharmaceutical compositions are formulated into tablets, tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In embodiments, the pharmaceutical compositions can comprise a) about 1 mg-8 mg of azelastine HCl (or other salt thereof) and b) about 0.2 mg to 4 mg of alprazolam or a) about 2 mg-6 mg of azelastine HCl (or other salt thereof) and b) about 0.2 mg to 1 mg of alprazolam or a) about 2 mg-4 mg of azelastine HCl (or other salt thereof) and b) about 0.2 mg to 0.4 mg of alprazolam, or any amount of azelastine or alprazolam within these ranges. Additional embodiments include pharmaceutical compositions comprising a) about up to and including any of 1 mg, 2 mg, 3 mg, 4 mg, 5 mg, 6 mg, 7 mg or 8 mg azelastine, such as azelastine HCl, or any amount within any of these ranges and b) about up to and including any of 0.2 mg, 0.3 mg, 0.4 mg, 0.5 mg 0.6 mg, 0.7 mg, 0.8 mg, 0.9 mg, 1 mg, 1.5 mg, 2 mg, 2.5 mg, 3 mg, 3.5 mg, or 4 mg alprazolam, or any salt thereof, or any amount within any of these ranges. For example, the compositions can comprise a) about 2 mg of azelastine HCl and b) about 0.4 mg of alprazolam HCl. Further, for example, compositions of the invention can comprise azelastine or a pharmaceutically acceptable salt of azelastine present in an amount in the range of about 1 mg to about 8 mg and alprazolam in an amount in the range of about 0.2 mg to about 4 mg. In embodiments, the amount of azelastine HCl (or other salt thereof) present in the composition can be equal to, more than, or less than the amount of alprazolam present in the composition. In embodiments, the amount of azelastine HCl (and/or other salt thereof) present in the composition can be 2 times as much, or 3 times as much, or 4, 5, 6, 7, 8, 9, 10, 15, 20, 25, 30, 35, 40, 45, or 50 times as much as the amount of alprazolam present in the composition, or vice versa. Any one or more of the compositions of the invention can be used with any one or more the methods of the invention disclosed herein, or other methods of using the compositions.

It will be understood, that the amount of the pharmaceutical composition containing azelastine HCl and alprazolam actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

The pharmaceutical compositions, pharmaceutical dosage forms, and tablets containing azelastine, such as azelastine HCl, and alprazolam as described herein are administered to a patient suffering from one or more psychiatric disorders such as MDD, GAD, panic disorder, agitation, SAD, MCD, OCD, PDD, SAD, dysthymia, childhood enuresis, bipolar disorder, PSD or SDRA, by administration (such as oral administration) once daily, twice daily, up to four times a day, once every other day, once a week, two times a week, three times a week, four times a week, or five times a week, or combinations thereof.

In embodiments, patients are administered the pharmaceutical composition(s) with a therapeutic effective daily dosage of azelastine (such as azelastine HCl) in the range of about 1 mg to about 8 mg and alprazolam or salt thereof in an amount in the range of about 0.2 mg to about 4 mg.

In embodiments, the pharmaceutical dosage forms and tablets of pharmaceutical compositions containing azelastine, such as azelastine HCl, and alprazolam as described herein are effective in reversing, reducing, alleviating, and/or treating one or more symptoms in patients with one or more psychiatric disorders such as MDD, GAD, panic disorder, agitation, SAD, MCD, OCD, PDD, SAD, dysthymia, childhood enuresis, bipolar disorder, PSD, or SDRA in about 1-8 weeks, such as within 1, 2, 3, 4, 5, 6, 7, or 8 weeks, or any range in between.

The following Examples are illustrative and should not be interpreted to limit the scope of the claimed subject matter.

Example 1

A 50 year old male patient had generalized anxiety disorder, panic disorder, and agitation. He was treated with different doses of fluoxetine alone for 4 months, sertraline of SSRIs alone for 6 months, and alprazolam (2.0 mg/daily) of benzodiazepines alone for 4 months but had no significant clinical improvement with any of these treatments. When all of his symptoms worsened, he was given a composition of alprazolam of 0.4 mg and azelastine of 2 mg once daily for 2 weeks, his symptoms started having a dramatic improvement. By 6 weeks of the treatment, he showed no symptoms of agitation and panic disorder and his anxiety disorder was reduced by more than 80%. Because azelastine is approved for the treatment of allergic rhinitis and asthma and has never been used to treat patients with depression or anxiety, this dramatic clinical outcome from this composition is unexpected. Although the inventors do not intend to be bound by this theory, it is believed that azelastine's anti-inflammatory action by suppressing release of cytokines, such as IL-1, IL-6, TNF-α and INF-α, in the CNS system may help alprazolam effectively bind to GABAA-benzodiazepine receptor complex which creates an effective presence of GABA to inhibit the action of several connected brain structures and further results in slowing of brain activity. This way of activating the GABA system may interact more effectively with other neurotransmitter systems, including noradrenergic, serotonergic, cholinergic, and opioidergic systems. Further, azelastine's anti-inflammatory action may help alprazolam interact in more effective ways with the serotonergic and noradrenergic pathways to the limbic system and brain stem structures. This composition of two mechanisms of action for two different classes of diseases provided a new solution for treating psychiatric diseases which are incurable by other options, such traditional SSRIs, NSRIs, benzodiazepines, and the like alone.

Example 2

A 52 year old female patient had generalized anxiety disorder, agitation and insomnia for 8 months and no treatment had been effective, including SSRIs or benzodiazepines (such as 2.0 mg/daily alprazolam) alone, before she was treated with a composition of alprazolam of 0.4 mg and azelastine of 2 mg once daily. After 2 weeks, she exhibited dramatic clinical improvement and showed no symptoms of agitation and her anxiety disorder was reduced by more than 50%. The inventors believe the hypothesis as explained in example 1 above is applicable here as well. In this case, the composition of two mechanisms of action for two different classes of diseases provided a new solution for treating her generalized anxiety diseases and agitation along with insomnia which could not be treated with other options, such traditional SSRIs, NSRIs, benzodiazepines, and the like alone.

Example 3

A 78 year old male patient had major depressive disorder and agitation for about 2 years and no treatment, including fluoxetine alone from SSRIs or alprazolam (2.0 mg/daily) alone from benzodiazepines, had been effective before he was treated with a composition of alprazolam of 0.4 mg and azelastine of 2 mg twice daily. After 4 weeks of treatment, he exhibited dramatic clinical improvement, showed no symptoms of agitation, and his major depressive disorder was reduced by more than 50%. The inventors believe the hypothesis as explained in example 1 above is applicable here as well. In this case, the composition of two mechanisms of action for two different classes of diseases provided a new solution for treating his major depressive disorder and agitation which could not be treated with other options, such traditional SSRIs, NSRIs, benzodiazepines, and the like alone.

REFERENCES

U.S. Pat. No. 9,308,212 (Apr. 12, 2016, Los), U.S. Pat. No. 8,865,733 (Oct. 21, 2014, Felder), U.S. Pat. No. 8,168,625 (May 1, 2012, Vandoni, et al), U.S. Pat. No. 9,919,050 (Mar. 20, 2018, Dang, et al); U.S. Pat. No. 9,901,585 (Feb. 27, 2018, Lulla, et al), U.S. Pat. No. 8,859,531 (Oct. 14, 2014, Lee, et al), U.S. Pat. No. 8,758,816 (Jun. 24, 2014, Fuge, et al), U.S. Pat. No. 8,318,709 (Nov. 27, 2012, Lulla, et al), U.S. Pat. No. 8,304,405 (Nov. 6, 2012, Lulla, et al), U.S. Pat. No. 8,168,620 (May 1, 2012, Lulla, et al), U.S. Pat. No. 8,071,073 (Dec. 6, 2011, Dang, et al), U.S. Pat. No. 7,022,687 (Apr. 4, 2006, Szelenyl, et al), U.S. Pat. No. 6,017,909 (Jan. 25, 2000, Hettche, et al), U.S. Pat. No. 5,994,357 (Nov. 30, 1999, Theoharides), U.S. Pat. No. 5,086,050 (Feb. 4, 1992, Hettche, et al), and U.S. Pat. No. 5,068,233 (Nov. 26, 1991, Achterrath-Tuckerman, et al.)
Joris C. Verster and Edmund R. Volkerts, 2004. Clinical Pharmacology, Clinical Efficacy, and Behavioral Toxicity of Alprazolam: A Review of the Literature. CNS Drug Reviews, Vol. 10, No. 1, pp. 45-76.
Zahid Sadek Chowdhury, 2016 The Effect of Chronic Alprazolam Intake on Memory, Attention, and Psychomotor Performance in Healthy Human Male Volunteers. Exp. Opin. Pharmacother, 6:1967-87.
Geoffrey K. Isbister, et al. 2004. Alprazolam is relatively more toxic than other benzodiazepines in overdose. British Journal of Clinical Pharmacology, Vol 58: 88-98.
J A Fawcett, H M Kravitz, 1982. Alprazolam: Pharmacokinetics, Clinical Efficacy, and Mechanism of Action. Pharmacotherapy, 2 (5): 243-54.
James P. Zacnya, Judith A. Paiceb, and Dennis W. Coalson, 2012. Separate and combined psychopharmacological effects of alprazolam and oxycodone in healthy volunteers, 2012 Aug. 1; 124(3): 274-282.
Danilo Nader and Linda Gowing, 2020. Is Long-Term Benzodiazepine Use a Risk Factor for Cognitive Decline? Results of a Systematic Review. J Addiction. January 23. doi: 10.1155/2020/1569456.
Simon F Crowe, Elizabeth K Stranks, 2018. The Residual Medium and Long-term Cognitive Effects of Benzodiazepine Use: An Updated Meta-analysis. Arch Clin Neuropsychol. 2018 Nov. 1; 33 (7): 901-911.
Ruihua Hou, 2017, Peripheral inflammatory cytokines and immune balance in Generalized Anxiety Disorder: case-controlled study. Brain Behav Immun. 2017 May; 62: 212-218.
Michelle Guignet, 2020, Persistent behavior deficits, neuroinflammation, and oxidative stress in a rat model of acute organophosphate intoxication, Vol 133, January 2020, 104431
Chun-Hong Liu, 2019, Role of inflammation in depression relapse, Journal of Neuroinflammation (2019) 16:90 limit the scope of the claimed subject matter.
Jovana Vojvodic, et al, 2019, The Impact of Immunological Factors on Depression Treatment—Relation Between Antidepressants and Immunomodulation Agents, Macedonian Journal of Medical Sciences. 2019 Sep. 30; 7(18): 3064-3069.
F. C. Bennett and A. V. Molofsky, 2019, The immune system and psychiatric disease: a basic science perspective, Clinical and Experimental Immunology, 197: 294-307
Ruihua Hou and David S. Baldwin, 2012, A neuroimmunological perspective on anxiety disorders, Human Psychopharmacol Clin Exp. Vol 27: 6-14.
N Kappelmann, G Lewis, R Dantzer, P B Jones and G M Khandaker, 2018, Antidepressant activity of anti-cytokine treatment: a systematic review and meta-analysis of clinical trials of chronic inflammatory conditions, Molecular Psychiatry. Vol. 23, 335-343.
A. Atri, S. D. Rountree, O. L. Lopez, and R. S. Doody, 2018, Impact of Mast Cells in Depression Disorder: Inhibitory Effect of IL-37 (New Frontiers). Immunol Res, vol. 66 (3), 323-331 June 2018.
Sung Ho Maeng and Heeok Hong, 2019, Inflammation as the Potential Basis in Depression. Int Neurourol J 2019; Vol 23 (Suppl 2): S63-71.
Ole Köhler, et al. van Hoven P T, Kaufman A, Carr W W. Inflammation in Depression and the Potential for Anti-Inflammatory Treatment. Current Neuropharmacology, 2016, 14, 732-742.
Anzela Niraula et al. 2019, Interleukin-6 Induced by Social Stress Promotes a Unique Transcriptional Signature in the Monocytes That Facilitate Anxiety. Biol Psychiatry 85 (8), 679-689 2019 Apr. 15.
M Catena-Dell'Osso, et al, 2011, Inflammatory and Neurodegenerative Pathways in Depression: A New Avenue for Antidepressant Development? Curr Med Chem. 18 (2), 245-55.

Duraisamy Kempuraj, et al. 2017, Mast Cell Activation in Brain Injury, Stress, and Post-traumatic Stress Disorder and Alzheimer's Disease, Front. Neurosci. 11:703. doi: 10.3389/fnins.2017.00703.

S Georgin-Lavialle et al. 2016, Mast Cells' Involvement in Inflammation Pathways Linked to Depression: Evidence in Mastocytosis. Mol Psychiatry. 21 (11), 1511-1516 November 2016.

Sang Won Jeon, Yong Ku Kim, 2016, Detrimental effect of preservative in eye drops: Neuroinflammation and cytokine abnormality in major depression: Cause or consequence in that illness? World Journal of Psychiatry, 2016 Sep. 22; 6(3): 283-293.

Romain Troubat et al, 2020, Neuroinflammation and Depression: A Review. Eur J Neurosci. 2020 Mar. 9 DOI: 10.1111/ejn.14720.

Ja Wook Kooa, et al, 2010, Nuclear factor-κB is a critical mediator of stress impaired neurogenesis and depressive behavior. PNAS, Feb. 9, 2010, Vol. 107 (6) 2669-2674.

Patricia B Williams, Elizabeth Crandall and John D Sheppard, 2010, Azelastine hydrochloride, a dual-acting anti-inflammatory ophthalmic solution, for treatment of allergic conjunctivitis. Clinical Ophthalmology 2010:4 993-1001

Casale T. The interaction of azelastine with human lung histamine H1, beta, and muscarinic receptor-binding sites. J Allergy Clin Immunol. 1989; 83:771-776.

Hazama H, Nakajima T, Hisada T, Hamada E, Omata M, Kurachi Y. Effects of azelastine on membrane currents in tracheal smooth muscle cells isolated from the guinea-pig. Eur J Pharmacol. 1994; 259: 143-150.

Szelenyi I, Achterrath-Tuckermann U, Schmidt J, Minker E, Paegelow I, Werner H. Azelastine: A multifaceted drug for asthma therapy. Agents Actions Suppl. 1991; 34:295-311.

Galatowicz G, Ajayi Y, Stern M E, Calder V L. Ocular antiallergic compounds selectively inhibit human mast cell cytokines in vitro and conjunctival cell infiltration in vivo. Clin Exp Allergy. 2007; 37:1648-1656.

Ciprandi G, Pronzato C, Passalacqua G, et al. Topical azelastine reduces eosinophil activation and intercellular adhesion molecule-1 expression on nasal epithelial cells: An antiallergic activity. J Allergy Clin Immunol. 1996; 98(6 Pt 1):1088-1096.

Simons F E, Simons K J. Clinical pharmacology of new histamine H1 receptor antagonist. Clin Pharmacokinet. 1999; 36:329-352.

Aiko Hatakeyama, 2008, Azelastine hydrochloride on behavioral and psychological symptoms and activities of daily living in dementia patients. Geriatr Gerontol Int 2008; 8: 59-61

Duraisamy Kempuraj, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 November 2003.

Kazunori Yoneda, et al. 1997, Suppression by Azelastine Hydrochloride of NF-KB Activation Involved in Generation of Cytokines and Nitric Oxide. Japanese Journal of Pharmacology, 73: 145-53.

Loyd Allen, Ansel's Pharmaceutical Dosage Forms and Drug Delivery Systems, Tenth (2013).

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A pharmaceutical composition, comprising:
   azelastine or a pharmaceutically acceptable salt of azelastine, wherein the azelastine or the pharmaceutically acceptable salt of azelastine is present in the pharmaceutical composition in an amount of about 2 mg;
   alprazolam, wherein the alprazolam is present in the pharmaceutical composition, and is present in an amount of about 0.4 mg;
   and one or more pharmaceutically acceptable excipients.

2. The pharmaceutical composition of claim 1, wherein the pharmaceutically acceptable salt of azelastine is azelastine hydrochloride.

3. The pharmaceutical composition of claim 1, wherein the pharmaceutical composition is formulated as an oral pharmaceutical dosage form.

4. The pharmaceutical composition of claim 3, wherein the oral pharmaceutical dosage form is a solid form or a liquid form.

5. A pharmaceutical composition, comprising:
   azelastine or a pharmaceutically acceptable salt of azelastine, wherein the azelastine or pharmaceutically acceptable salt of azelastine is present in the pharmaceutical composition in an amount of about 1 mg; and
   alprazolam, wherein the alprazolam is present in the pharmaceutical composition in an amount of about 0.2 mg.

6. The pharmaceutical composition of claim 5, wherein the pharmaceutically acceptable salt of azelastine is azelastine hydrochloride.

7. The pharmaceutical composition of claim 5, wherein the pharmaceutical composition is formulated as an oral pharmaceutical dosage form.

8. The pharmaceutical composition of claim 7, wherein the oral pharmaceutical dosage form is a solid form or a liquid form.

* * * * *